(12) United States Patent
Schneider et al.

(10) Patent No.: US 10,194,962 B2
(45) Date of Patent: *Feb. 5, 2019

(54) MATRIX IMPLANT

(71) Applicant: SI-Bone Inc., San Jose, CA (US)

(72) Inventors: Bret W. Schneider, Morgan Hill, CA (US); Roxanne Simon, San Jose, CA (US); Derek Lindsey, Santa Clara, CA (US); Scott A. Yerby, Montara, CA (US)

(73) Assignee: SI-Bone Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/593,208

(22) Filed: May 11, 2017

(65) Prior Publication Data

US 2017/0296244 A1    Oct. 19, 2017

Related U.S. Application Data

(63) Continuation of application No. 14/859,005, filed on Sep. 18, 2015, now Pat. No. 9,662,157.

(Continued)

(51) Int. Cl.
*A61F 2/44* (2006.01)
*A61B 17/84* (2006.01)
(Continued)

(52) U.S. Cl.
CPC .......... *A61B 17/84* (2013.01); *A61B 17/7055* (2013.01); *A61F 2/44* (2013.01); *A61F 2002/2839* (2013.01); *A61F 2002/30115* (2013.01); *A61F 2002/30149* (2013.01); *A61F 2002/30154* (2013.01); *A61F 2002/30156* (2013.01); *A61F 2002/30171* (2013.01); *A61F 2002/30604* (2013.01); *A61F 2002/30995* (2013.01); *A61F 2002/4495* (2013.01)

(58) Field of Classification Search
CPC .................................. A61B 17/7064–17/7071
See application file for complete search history.

(56) References Cited

U.S. PATENT DOCUMENTS

| 1,951,278 A | 3/1934 | Ericsson |
| 2,136,471 A | 11/1938 | Schneider |

(Continued)

FOREIGN PATENT DOCUMENTS

| CN | 1128944 A | 8/1996 |
| CN | 1190882 A | 8/1998 |

(Continued)

OTHER PUBLICATIONS

Acumed; Acutrak Headless Compressioin Screw (product information); 12 pgs; © 2005; retrieved Sep. 25, 2014 from http://www.rcsed.ac.uk/fellows/Ivanrensburg/classification/surgtech/acumed/manuals/acutrak-brochure%200311.pdf.

(Continued)

*Primary Examiner* — Eduardo C Robert
*Assistant Examiner* — Michelle C Eckman
(74) *Attorney, Agent, or Firm* — Shay Glenn LLP

(57) ABSTRACT

Implants for the fusion or fixation of two bone segments are described. For example, the implants can be used for the fusion or fixation of the sacroiliac joint. The implants can have a matrix structure, have a rectilinear cross-sectional area, and have a curvature.

7 Claims, 10 Drawing Sheets

Related U.S. Application Data

(60) Provisional application No. 62/052,379, filed on Sep. 18, 2014.

(51) Int. Cl.
*A61B 17/70* (2006.01)
*A61F 2/30* (2006.01)
*A61F 2/28* (2006.01)

(56) References Cited

U.S. PATENT DOCUMENTS

| | | | |
|---|---|---|---|
| 2,243,717 A | 5/1941 | Moreira | |
| 2,414,882 A | 7/1947 | Longfellow | |
| 2,562,419 A | 7/1951 | Ferris | |
| 2,675,801 A * | 4/1954 | Bambara et al. | A61B 17/72 606/62 |
| 2,697,433 A | 12/1954 | Zehnder | |
| 3,076,453 A | 2/1963 | Tronzo | |
| 3,506,982 A | 4/1970 | Steffee | |
| 3,694,821 A | 10/1972 | Moritz | |
| 3,709,218 A | 1/1973 | Halloran | |
| 3,744,488 A | 7/1973 | Cox | |
| 4,059,115 A | 11/1977 | Jumashev et al. | |
| 4,156,943 A | 6/1979 | Collier | |
| 4,292,964 A | 10/1981 | Ulrich | |
| 4,341,206 A | 7/1982 | Perrett et al. | |
| 4,344,190 A | 8/1982 | Lee et al. | |
| 4,399,813 A | 8/1983 | Barber | |
| 4,423,721 A | 1/1984 | Otte et al. | |
| 4,475,545 A | 10/1984 | Ender | |
| 4,501,269 A | 2/1985 | Bagby | |
| 4,569,338 A | 2/1986 | Edwards | |
| 4,612,918 A | 9/1986 | Slocum | |
| 4,622,959 A | 11/1986 | Marcus | |
| 4,630,601 A | 12/1986 | Harder et al. | |
| 4,638,799 A | 1/1987 | Moore | |
| 4,657,550 A | 4/1987 | Daher | |
| 4,743,256 A | 5/1988 | Brantigan | |
| 4,773,402 A | 9/1988 | Asher et al. | |
| 4,787,378 A | 11/1988 | Sodhi | |
| 4,790,303 A | 12/1988 | Steffee | |
| 4,834,757 A | 5/1989 | Brantigan | |
| 4,846,162 A | 7/1989 | Moehring | |
| 4,877,019 A | 10/1989 | Vives | |
| 4,878,915 A | 11/1989 | Brantigan | |
| 4,898,186 A | 2/1990 | Ikada et al. | |
| 4,904,261 A | 2/1990 | Dove et al. | |
| 4,950,270 A | 8/1990 | Bowman et al. | |
| 4,961,740 A | 10/1990 | Ray et al. | |
| 4,969,888 A | 11/1990 | Scholten et al. | |
| 4,981,481 A | 1/1991 | Kranz et al. | |
| 5,034,011 A | 7/1991 | Howland | |
| 5,034,013 A | 7/1991 | Kyle et al. | |
| 5,035,697 A | 7/1991 | Frigg | |
| 5,041,118 A | 8/1991 | Wasilewski | |
| 5,053,035 A | 10/1991 | McLaren | |
| 5,059,193 A | 10/1991 | Kuslich | |
| 5,066,296 A | 11/1991 | Chapman et al. | |
| 5,102,414 A | 4/1992 | Kirsch | |
| 5,108,397 A | 4/1992 | White | |
| 5,122,141 A | 6/1992 | Simpson et al. | |
| 5,139,498 A | 8/1992 | Astudillo Ley | |
| 5,139,500 A | 8/1992 | Schwartz | |
| 5,147,367 A | 9/1992 | Ellis | |
| 5,147,402 A | 9/1992 | Bohler et al. | |
| 5,190,551 A | 3/1993 | Chin et al. | |
| 5,197,961 A | 3/1993 | Castle | |
| 5,242,444 A | 9/1993 | MacMillan | |
| 5,298,254 A | 3/1994 | Prewett et al. | |
| 5,334,205 A | 8/1994 | Cain | |
| 5,380,325 A | 1/1995 | Lahille et al. | |
| 5,390,683 A | 2/1995 | Pisharodi | |
| 5,433,718 A | 7/1995 | Brinker | |
| 5,443,466 A | 8/1995 | Shah | |
| 5,458,638 A | 10/1995 | Kuslich et al. | |
| 5,470,334 A | 11/1995 | Ross et al. | |
| 5,480,402 A | 1/1996 | Kim | |
| 5,569,249 A | 10/1996 | James et al. | |
| 5,591,235 A | 1/1997 | Kuslich | |
| 5,593,409 A | 1/1997 | Michelson | |
| 5,609,635 A * | 3/1997 | Michelson | A61F 2/30744 606/247 |
| 5,609,636 A | 3/1997 | Kohrs et al. | |
| 5,626,616 A | 5/1997 | Speece | |
| 5,643,264 A | 7/1997 | Sherman et al. | |
| 5,645,599 A | 7/1997 | Samani | |
| 5,658,337 A | 8/1997 | Kohrs et al. | |
| 5,667,510 A | 9/1997 | Combs | |
| 5,669,909 A | 9/1997 | Zdeblick et al. | |
| 5,672,178 A | 9/1997 | Petersen | |
| 5,683,391 A | 11/1997 | Boyd | |
| 5,709,683 A | 1/1998 | Bagby | |
| 5,713,904 A | 2/1998 | Errico et al. | |
| 5,716,358 A | 2/1998 | Ochoa et al. | |
| 5,725,581 A | 3/1998 | Brånemark | |
| 5,743,912 A | 4/1998 | LaHille et al. | |
| 5,759,035 A | 6/1998 | Ricci | |
| 5,766,174 A | 6/1998 | Perry | |
| 5,766,252 A | 6/1998 | Henry et al. | |
| 5,766,261 A | 6/1998 | Neal et al. | |
| 5,788,699 A | 8/1998 | Bobst et al. | |
| 5,800,440 A | 9/1998 | Stead | |
| 5,868,749 A | 2/1999 | Reed | |
| 5,897,556 A * | 4/1999 | Drewry | A61B 17/8085 606/247 |
| 5,928,239 A | 7/1999 | Mirza | |
| 5,941,885 A | 8/1999 | Jackson | |
| 5,961,522 A | 10/1999 | Mehdizadeh | |
| 5,961,554 A | 10/1999 | Janson et al. | |
| 6,010,507 A | 1/2000 | Rudloff | |
| 6,015,409 A | 1/2000 | Jackson | |
| 6,053,916 A | 4/2000 | Moore | |
| 6,056,749 A | 5/2000 | Kuslich | |
| 6,086,589 A | 7/2000 | Kuslich et al. | |
| 6,096,080 A | 8/2000 | Nicholson et al. | |
| 6,120,504 A | 9/2000 | Brumback et al. | |
| 6,143,031 A | 11/2000 | Knothe et al. | |
| 6,197,062 B1 | 3/2001 | Fenlin | |
| 6,210,442 B1 | 4/2001 | Wing et al. | |
| 6,214,049 B1 | 4/2001 | Gayer et al. | |
| 6,221,074 B1 | 4/2001 | Cole et al. | |
| 6,224,607 B1 | 5/2001 | Michelson | |
| 6,241,732 B1 | 6/2001 | Overaker et al. | |
| 6,264,657 B1 | 7/2001 | Urbahns et al. | |
| 6,270,528 B1 | 8/2001 | McKay | |
| 6,287,343 B1 | 9/2001 | Kuslich et al. | |
| 6,302,885 B1 | 10/2001 | Essiger | |
| 6,302,914 B1 | 10/2001 | Michelson | |
| 6,306,140 B1 | 10/2001 | Siddiqui | |
| 6,319,253 B1 | 11/2001 | Ackeret et al. | |
| 6,406,498 B1 | 6/2002 | Tormala et al. | |
| 6,409,768 B1 | 6/2002 | Tepic et al. | |
| 6,451,020 B1 | 9/2002 | Zucherman et al. | |
| 6,471,707 B1 | 10/2002 | Miller et al. | |
| 6,485,518 B1 | 11/2002 | Cornwall et al. | |
| 6,497,707 B1 | 12/2002 | Bowman et al. | |
| 6,517,541 B1 | 2/2003 | Sesic | |
| 6,520,969 B2 | 2/2003 | Lambrecht et al. | |
| 6,524,314 B1 | 2/2003 | Dean et al. | |
| 6,527,775 B1 | 3/2003 | Warburton | |
| 6,558,386 B1 | 5/2003 | Cragg | |
| 6,565,566 B1 | 5/2003 | Wagner et al. | |
| 6,575,899 B1 | 6/2003 | Foley et al. | |
| 6,575,991 B1 | 6/2003 | Chesbrough et al. | |
| 6,579,293 B1 | 6/2003 | Chandran | |
| 6,582,431 B1 | 6/2003 | Ray | |
| 6,595,998 B2 | 7/2003 | Johnson et al. | |
| 6,602,293 B1 | 8/2003 | Biermann et al. | |
| 6,605,090 B1 | 8/2003 | Trieu et al. | |
| 6,607,530 B1 | 8/2003 | Carl et al. | |
| 6,620,163 B1 | 9/2003 | Michelson | |
| 6,635,059 B2 | 10/2003 | Randall et al. | |
| 6,666,868 B2 | 12/2003 | Fallin | |
| 6,669,529 B1 | 12/2003 | Scaries | |

(56) References Cited

U.S. PATENT DOCUMENTS

| | | |
|---|---|---|
| 6,673,075 B2 | 1/2004 | Santilli |
| 6,692,501 B2 | 2/2004 | Michelson |
| 6,723,099 B1 | 4/2004 | Goshert |
| 6,740,118 B2 | 5/2004 | Eisermann et al. |
| 6,743,257 B2 | 6/2004 | Castro |
| D493,533 S * | 7/2004 | Blain .......................... D24/155 |
| 6,793,656 B1 | 9/2004 | Mathews |
| 6,827,740 B1 | 12/2004 | Michelson |
| 6,984,235 B2 | 1/2006 | Huebner |
| 6,991,461 B2 | 1/2006 | Gittleman |
| 7,118,579 B2 | 10/2006 | Michelson |
| 7,175,663 B1 | 2/2007 | Stone |
| 7,211,085 B2 | 5/2007 | Michelson |
| 7,223,269 B2 | 5/2007 | Chappuis |
| 7,314,488 B2 | 1/2008 | Reiley |
| 7,335,205 B2 | 2/2008 | Aeschlimann et al. |
| 7,338,500 B2 | 3/2008 | Chappuis |
| 7,452,359 B1 | 11/2008 | Michelson |
| 7,452,369 B2 | 11/2008 | Barry |
| 7,481,831 B2 | 1/2009 | Bonutti |
| 7,527,649 B1 * | 5/2009 | Blain .................... A61F 2/4455 623/17.11 |
| 7,534,254 B1 | 5/2009 | Michelson |
| 7,537,616 B1 * | 5/2009 | Branch ................. A61F 2/2846 623/17.11 |
| 7,569,054 B2 | 8/2009 | Michelson |
| 7,569,059 B2 | 8/2009 | Cerundolo |
| 7,601,155 B2 | 10/2009 | Petersen |
| 7,648,509 B2 | 1/2010 | Stark |
| 7,686,805 B2 | 3/2010 | Michelson |
| 7,699,852 B2 | 4/2010 | Frankel et al. |
| 7,708,761 B2 | 5/2010 | Petersen |
| 7,727,235 B2 | 6/2010 | Contiliano et al. |
| 7,758,646 B2 | 7/2010 | Khandkar et al. |
| 7,780,704 B2 | 8/2010 | Markworth et al. |
| 7,837,735 B2 | 11/2010 | Malone |
| 7,850,732 B2 | 12/2010 | Heinz |
| 7,857,832 B2 | 12/2010 | Culbert et al. |
| 7,887,565 B2 | 2/2011 | Michelson |
| 7,901,439 B2 | 3/2011 | Horton |
| 7,909,832 B2 | 3/2011 | Michelson |
| 7,922,765 B2 | 4/2011 | Reiley |
| 7,942,879 B2 | 5/2011 | Christie et al. |
| 8,052,728 B2 | 11/2011 | Hestad |
| 8,062,365 B2 * | 11/2011 | Schwab ................ A61F 2/2846 623/17.11 |
| 8,066,705 B2 | 11/2011 | Michelson |
| 8,066,709 B2 | 11/2011 | Michelson |
| 8,080,046 B2 | 12/2011 | Suddaby |
| 8,142,481 B2 | 3/2012 | Warnick |
| 8,142,503 B2 | 3/2012 | Malone |
| 8,162,981 B2 | 4/2012 | Vestgaarden |
| 8,202,305 B2 | 6/2012 | Reiley |
| 8,308,779 B2 | 11/2012 | Reiley |
| 8,317,862 B2 | 11/2012 | Troger et al. |
| 8,348,950 B2 | 1/2013 | Assell et al. |
| 8,388,667 B2 | 3/2013 | Reiley et al. |
| 8,394,129 B2 | 3/2013 | Morgenstern Lopez |
| 8,398,635 B2 | 3/2013 | Vaidya |
| 8,414,648 B2 | 4/2013 | Reiley |
| 8,425,570 B2 | 4/2013 | Reiley |
| 8,430,930 B2 | 4/2013 | Hunt |
| 8,439,925 B2 | 5/2013 | Marino et al. |
| 8,444,693 B2 | 5/2013 | Reiley |
| 8,470,004 B2 | 6/2013 | Reiley |
| 8,529,608 B2 | 9/2013 | Terrill et al. |
| 8,608,802 B2 | 12/2013 | Bagga et al. |
| D697,209 S | 1/2014 | Walthall et al. |
| 8,641,737 B2 | 2/2014 | Matthis et al. |
| 8,672,986 B2 | 3/2014 | Klaue et al. |
| 8,734,462 B2 | 5/2014 | Reiley et al. |
| 8,778,026 B2 | 7/2014 | Mauldin |
| 8,840,623 B2 | 9/2014 | Reiley |
| 8,840,651 B2 | 9/2014 | Reiley |
| 8,858,601 B2 | 10/2014 | Reiley |
| 8,920,477 B2 | 12/2014 | Reiley |
| 8,945,190 B2 | 2/2015 | Culbert et al. |
| 8,945,193 B2 | 2/2015 | Kirschman |
| 8,951,254 B2 | 2/2015 | Mayer et al. |
| 8,951,293 B2 | 2/2015 | Glazer et al. |
| 8,951,295 B2 | 2/2015 | Matityahu et al. |
| 8,961,571 B2 | 2/2015 | Lee et al. |
| 8,986,348 B2 | 3/2015 | Reiley |
| 9,039,743 B2 | 5/2015 | Reiley |
| 9,044,321 B2 | 6/2015 | Mauldin et al. |
| 9,060,876 B1 * | 6/2015 | To .......................... A61F 2/442 |
| 9,089,371 B1 | 7/2015 | Faulhaber |
| D738,498 S | 9/2015 | Frey et al. |
| 9,131,955 B2 | 9/2015 | Swofford |
| 9,149,286 B1 | 10/2015 | Greenhalgh et al. |
| 9,198,676 B2 | 12/2015 | Pilgeram et al. |
| 9,220,535 B2 | 12/2015 | Röbling et al. |
| 9,314,348 B2 | 4/2016 | Emstad |
| 9,358,057 B1 | 6/2016 | Whipple et al. |
| 9,375,243 B1 | 6/2016 | Vestgaarden |
| 9,375,323 B2 | 6/2016 | Reiley |
| 9,452,065 B1 | 9/2016 | Lawson |
| 9,486,264 B2 | 11/2016 | Reiley et al. |
| 9,492,201 B2 | 11/2016 | Reiley |
| 9,492,284 B2 | 11/2016 | Ginn et al. |
| 9,498,264 B2 | 11/2016 | Harshman et al. |
| 9,510,872 B2 | 12/2016 | Donner et al. |
| 9,517,095 B2 | 12/2016 | Vaidya |
| 9,522,028 B2 | 12/2016 | Warren et al. |
| 9,526,548 B2 | 12/2016 | Asfora |
| 9,554,909 B2 | 1/2017 | Donner |
| 9,561,063 B2 | 2/2017 | Reiley |
| 9,566,095 B2 | 2/2017 | Lorio |
| 9,566,100 B2 | 2/2017 | Asfora |
| 9,592,131 B2 | 3/2017 | Sandstrom et al. |
| 9,603,613 B2 | 3/2017 | Schoenefeld et al. |
| 9,615,856 B2 | 4/2017 | Arnett et al. |
| 9,622,783 B2 | 4/2017 | Reiley et al. |
| 9,636,226 B2 | 5/2017 | Hunt |
| 9,662,124 B2 | 5/2017 | Assell et al. |
| 9,662,128 B2 | 5/2017 | Reiley |
| 9,662,157 B2 | 5/2017 | Schneider et al. |
| 9,662,158 B2 | 5/2017 | Reiley |
| 9,675,394 B2 | 6/2017 | Reiley |
| 9,757,154 B2 | 9/2017 | Donner et al. |
| 9,763,695 B2 | 9/2017 | Mirda |
| 2001/0012942 A1 | 8/2001 | Estes et al. |
| 2001/0046518 A1 | 11/2001 | Sawhney |
| 2001/0047207 A1 * | 11/2001 | Michelson .............. A61F 2/446 623/17.11 |
| 2001/0049529 A1 | 12/2001 | Cachia et al. |
| 2002/0038123 A1 | 3/2002 | Visotsky et al. |
| 2002/0049497 A1 | 4/2002 | Mason |
| 2002/0077641 A1 | 6/2002 | Michelson |
| 2002/0082598 A1 | 6/2002 | Teitelbaum |
| 2002/0120275 A1 | 8/2002 | Schmieding et al. |
| 2002/0128652 A1 * | 9/2002 | Ferree ................ A61B 17/1671 623/17.11 |
| 2002/0143334 A1 | 10/2002 | von Hoffmann et al. |
| 2002/0143335 A1 | 10/2002 | von Hoffmann et al. |
| 2002/0151903 A1 | 10/2002 | Takei et al. |
| 2002/0169507 A1 | 11/2002 | Malone |
| 2002/0183858 A1 | 12/2002 | Contiliano et al. |
| 2002/0198527 A1 | 12/2002 | Mückter |
| 2003/0018336 A1 | 1/2003 | Vandewalle |
| 2003/0032961 A1 | 2/2003 | Pelo et al. |
| 2003/0050642 A1 | 3/2003 | Schmieding et al. |
| 2003/0065332 A1 | 4/2003 | TenHuisen et al. |
| 2003/0074000 A1 | 4/2003 | Roth et al. |
| 2003/0078660 A1 | 4/2003 | Clifford et al. |
| 2003/0083668 A1 | 5/2003 | Rogers et al. |
| 2003/0083688 A1 | 5/2003 | Simonson |
| 2003/0097131 A1 | 5/2003 | Schon et al. |
| 2003/0139815 A1 | 7/2003 | Grooms et al. |
| 2003/0181979 A1 | 9/2003 | Ferree |
| 2003/0181982 A1 | 9/2003 | Kuslich |
| 2003/0199983 A1 | 10/2003 | Michelson |
| 2003/0229358 A1 | 12/2003 | Errico et al. |
| 2003/0233146 A1 | 12/2003 | Grinberg et al. |

(56) References Cited

U.S. PATENT DOCUMENTS

| | | |
|---|---|---|
| 2003/0233147 A1 | 12/2003 | Nicholson et al. |
| 2004/0010315 A1* | 1/2004 | Song .................. A61F 2/44 623/17.16 |
| 2004/0024458 A1 | 2/2004 | Senegas et al. |
| 2004/0034422 A1 | 2/2004 | Errico et al. |
| 2004/0073216 A1 | 4/2004 | Lieberman |
| 2004/0073314 A1 | 4/2004 | White et al. |
| 2004/0082955 A1 | 4/2004 | Zirkle |
| 2004/0087948 A1 | 5/2004 | Suddaby |
| 2004/0097927 A1 | 5/2004 | Yeung et al. |
| 2004/0106925 A1 | 6/2004 | Culbert |
| 2004/0117022 A1 | 6/2004 | Marnay et al. |
| 2004/0127990 A1 | 7/2004 | Bartish, Jr. et al. |
| 2004/0138750 A1 | 7/2004 | Mitchell |
| 2004/0138753 A1 | 7/2004 | Ferree |
| 2004/0147929 A1 | 7/2004 | Biedermann et al. |
| 2004/0176287 A1 | 9/2004 | Harrison et al. |
| 2004/0176853 A1 | 9/2004 | Sennett et al. |
| 2004/0181282 A1 | 9/2004 | Zucherman et al. |
| 2004/0210221 A1 | 10/2004 | Kozak et al. |
| 2004/0225360 A1 | 11/2004 | Malone |
| 2004/0230305 A1* | 11/2004 | Gorensek ............. A61F 2/446 623/17.11 |
| 2004/0260286 A1 | 12/2004 | Ferree |
| 2004/0267369 A1 | 12/2004 | Lyons et al. |
| 2005/0015059 A1 | 1/2005 | Sweeney |
| 2005/0015146 A1 | 1/2005 | Louis et al. |
| 2005/0033435 A1 | 2/2005 | Belliard et al. |
| 2005/0049590 A1 | 3/2005 | Alleyne et al. |
| 2005/0055023 A1 | 3/2005 | Sohngen et al. |
| 2005/0075641 A1 | 4/2005 | Singhatat et al. |
| 2005/0080415 A1 | 4/2005 | Keyer et al. |
| 2005/0107878 A1 | 5/2005 | Conchy |
| 2005/0124993 A1 | 6/2005 | Chappuis |
| 2005/0131409 A1 | 6/2005 | Chervitz et al. |
| 2005/0137605 A1 | 6/2005 | Assell et al. |
| 2005/0143837 A1 | 6/2005 | Ferree |
| 2005/0149192 A1* | 7/2005 | Zucherman ........ A61B 17/1671 623/17.11 |
| 2005/0159749 A1 | 7/2005 | Levy et al. |
| 2005/0165398 A1 | 7/2005 | Reiley |
| 2005/0192572 A1 | 9/2005 | Abdelgany et al. |
| 2005/0228384 A1 | 10/2005 | Zucherman et al. |
| 2005/0246021 A1 | 11/2005 | Ringeisen et al. |
| 2005/0251146 A1 | 11/2005 | Martz et al. |
| 2005/0277940 A1 | 12/2005 | Neff |
| 2006/0036247 A1 | 2/2006 | Michelson |
| 2006/0036251 A1 | 2/2006 | Reiley |
| 2006/0054171 A1 | 3/2006 | Dall |
| 2006/0058793 A1 | 3/2006 | Michelson |
| 2006/0058800 A1 | 3/2006 | Ainsworth et al. |
| 2006/0062825 A1 | 3/2006 | Maccecchini |
| 2006/0084986 A1 | 4/2006 | Grinberg et al. |
| 2006/0089656 A1 | 4/2006 | Allard et al. |
| 2006/0111779 A1 | 5/2006 | Petersen |
| 2006/0129247 A1 | 6/2006 | Brown et al. |
| 2006/0142772 A1 | 6/2006 | Ralph et al. |
| 2006/0161163 A1 | 7/2006 | Shino |
| 2006/0178673 A1 | 8/2006 | Curran |
| 2006/0195094 A1 | 8/2006 | McGraw et al. |
| 2006/0217717 A1 | 9/2006 | Whipple |
| 2006/0241776 A1 | 10/2006 | Brown et al. |
| 2006/0271054 A1 | 11/2006 | Sucec et al. |
| 2006/0293662 A1 | 12/2006 | Boyer, II et al. |
| 2007/0027544 A1* | 2/2007 | McCord ............... A61F 2/447 623/17.11 |
| 2007/0049933 A1 | 3/2007 | Ahn et al. |
| 2007/0066977 A1 | 3/2007 | Assell et al. |
| 2007/0083265 A1 | 4/2007 | Malone |
| 2007/0088362 A1 | 4/2007 | Bonutti et al. |
| 2007/0093841 A1 | 4/2007 | Hoogland |
| 2007/0106383 A1* | 5/2007 | Abdou ................. A61B 17/70 623/17.11 |
| 2007/0149976 A1 | 6/2007 | Hale et al. |
| 2007/0156144 A1 | 7/2007 | Ulrich et al. |
| 2007/0156241 A1* | 7/2007 | Reiley ................ A61B 17/1615 623/17.11 |
| 2007/0156246 A1 | 7/2007 | Meswania et al. |
| 2007/0161989 A1 | 7/2007 | Heinz et al. |
| 2007/0219634 A1* | 9/2007 | Greenhalgh ....... A61B 17/8858 623/17.16 |
| 2007/0233146 A1 | 10/2007 | Henniges et al. |
| 2007/0250166 A1 | 10/2007 | McKay |
| 2007/0265621 A1 | 11/2007 | Matthis et al. |
| 2007/0270879 A1 | 11/2007 | Isaza et al. |
| 2008/0021454 A1 | 1/2008 | Chao et al. |
| 2008/0021455 A1 | 1/2008 | Chao et al. |
| 2008/0021456 A1 | 1/2008 | Gupta et al. |
| 2008/0021461 A1 | 1/2008 | Barker et al. |
| 2008/0021480 A1 | 1/2008 | Chin et al. |
| 2008/0065093 A1 | 3/2008 | Assell et al. |
| 2008/0065215 A1 | 3/2008 | Reiley |
| 2008/0109083 A1 | 5/2008 | Van Hoeck et al. |
| 2008/0140082 A1 | 6/2008 | Erdem et al. |
| 2008/0147079 A1 | 6/2008 | Chin et al. |
| 2008/0154374 A1 | 6/2008 | Labrom |
| 2008/0161810 A1 | 7/2008 | Melkent |
| 2008/0183204 A1* | 7/2008 | Greenhalgh ....... A61B 17/8858 606/198 |
| 2008/0234758 A1 | 9/2008 | Fisher et al. |
| 2008/0255562 A1 | 10/2008 | Gil et al. |
| 2008/0255618 A1 | 10/2008 | Fisher et al. |
| 2008/0255622 A1 | 10/2008 | Mickiewicz et al. |
| 2008/0255664 A1 | 10/2008 | Hogendijk et al. |
| 2008/0255666 A1 | 10/2008 | Fisher et al. |
| 2008/0255667 A1 | 10/2008 | Horton |
| 2008/0275454 A1 | 11/2008 | Geibel |
| 2008/0306554 A1 | 12/2008 | McKinley |
| 2009/0012529 A1 | 1/2009 | Blain et al. |
| 2009/0018660 A1 | 1/2009 | Roush |
| 2009/0024174 A1 | 1/2009 | Stark |
| 2009/0036927 A1 | 2/2009 | Vestgaarden |
| 2009/0043393 A1 | 2/2009 | Duggal et al. |
| 2009/0082869 A1 | 3/2009 | Slemker et al. |
| 2009/0099602 A1 | 4/2009 | Aflatoon |
| 2009/0099610 A1* | 4/2009 | Johnson ............. A61B 17/7055 606/86 R |
| 2009/0105770 A1 | 4/2009 | Berrevoets et al. |
| 2009/0118771 A1 | 5/2009 | Gonzalez-Hernandez |
| 2009/0131986 A1 | 5/2009 | Lee et al. |
| 2009/0138053 A1 | 5/2009 | Assell et al. |
| 2009/0157119 A1 | 6/2009 | Hale |
| 2009/0163920 A1 | 6/2009 | Hochschuler et al. |
| 2009/0187247 A1 | 7/2009 | Metcalf, Jr. et al. |
| 2009/0216238 A1 | 8/2009 | Stark |
| 2009/0270929 A1 | 10/2009 | Suddaby |
| 2009/0287254 A1 | 11/2009 | Nayet et al. |
| 2009/0312798 A1 | 12/2009 | Varela |
| 2009/0324678 A1 | 12/2009 | Thorne et al. |
| 2010/0016903 A1 | 1/2010 | Matityahu et al. |
| 2010/0022535 A1 | 1/2010 | Lee et al. |
| 2010/0076502 A1 | 3/2010 | Guyer et al. |
| 2010/0081107 A1 | 4/2010 | Bagambisa et al. |
| 2010/0094290 A1 | 4/2010 | Vaidya |
| 2010/0094295 A1 | 4/2010 | Schnieders et al. |
| 2010/0106194 A1 | 4/2010 | Bonutti et al. |
| 2010/0106195 A1 | 4/2010 | Serhan et al. |
| 2010/0114174 A1 | 5/2010 | Jones et al. |
| 2010/0114317 A1 | 5/2010 | Lambrecht et al. |
| 2010/0131011 A1 | 5/2010 | Stark |
| 2010/0145461 A1 | 6/2010 | Landry et al. |
| 2010/0160977 A1 | 6/2010 | Gephart et al. |
| 2010/0161061 A1* | 6/2010 | Hunt .................. A61B 17/1604 623/17.16 |
| 2010/0191292 A1 | 7/2010 | DeMeo et al. |
| 2010/0198267 A1 | 8/2010 | Vaidya |
| 2010/0268228 A1 | 10/2010 | Petersen |
| 2010/0280619 A1 | 11/2010 | Yuan et al. |
| 2010/0280622 A1 | 11/2010 | McKinley |
| 2010/0286778 A1 | 11/2010 | Eisermann et al. |
| 2010/0331851 A1 | 12/2010 | Huene |
| 2010/0331893 A1 | 12/2010 | Geist et al. |
| 2011/0009869 A1 | 1/2011 | Marino et al. |

(56) References Cited

U.S. PATENT DOCUMENTS

| | | |
|---|---|---|
| 2011/0022089 A1 | 1/2011 | Assell et al. |
| 2011/0029019 A1 | 2/2011 | Ainsworth et al. |
| 2011/0040362 A1 | 2/2011 | Godara et al. |
| 2011/0046737 A1 | 2/2011 | Teisen |
| 2011/0060373 A1 | 3/2011 | Russell et al. |
| 2011/0060375 A1 | 3/2011 | Bonutti |
| 2011/0066190 A1 | 3/2011 | Schaller et al. |
| 2011/0082551 A1* | 4/2011 | Kraus ............... A61F 2/30771 623/17.11 |
| 2011/0087294 A1* | 4/2011 | Reiley ............... A61B 17/1659 606/279 |
| 2011/0087296 A1* | 4/2011 | Reiley ............... A61B 17/1659 606/303 |
| 2011/0093020 A1 | 4/2011 | Wu |
| 2011/0098747 A1 | 4/2011 | Donner et al. |
| 2011/0098816 A1 | 4/2011 | Jacob et al. |
| 2011/0098817 A1 | 4/2011 | Eckhardt et al. |
| 2011/0106175 A1 | 5/2011 | Rezach |
| 2011/0118785 A1* | 5/2011 | Reiley ............... A61B 17/1615 606/264 |
| 2011/0118790 A1* | 5/2011 | Reiley ............... A61B 17/1615 606/279 |
| 2011/0118841 A1* | 5/2011 | Reiley ............... A61B 17/1615 623/17.11 |
| 2011/0125268 A1* | 5/2011 | Reiley ............... A61B 17/1615 623/17.11 |
| 2011/0153018 A1 | 6/2011 | Walters et al. |
| 2011/0160866 A1 | 6/2011 | Laurence et al. |
| 2011/0178561 A1 | 7/2011 | Roh |
| 2011/0184518 A1* | 7/2011 | Trieu ............... A61B 17/562 623/17.11 |
| 2011/0184519 A1 | 7/2011 | Trieu |
| 2011/0184520 A1 | 7/2011 | Trieu |
| 2011/0196372 A1 | 8/2011 | Murase |
| 2011/0230966 A1 | 9/2011 | Trieu |
| 2011/0238181 A1 | 9/2011 | Trieu |
| 2011/0257755 A1 | 10/2011 | Bellemere et al. |
| 2011/0264229 A1* | 10/2011 | Donner ............... A61F 2/30988 623/18.11 |
| 2011/0295272 A1 | 12/2011 | Assell et al. |
| 2011/0295370 A1 | 12/2011 | Suh et al. |
| 2011/0313532 A1* | 12/2011 | Hunt ............... A61F 2/30767 623/18.11 |
| 2012/0083887 A1 | 4/2012 | Purcell et al. |
| 2012/0095560 A1* | 4/2012 | Donner ............... A61F 2/30988 623/17.11 |
| 2012/0101530 A1 | 4/2012 | Robling et al. |
| 2012/0179256 A1 | 7/2012 | Reiley |
| 2012/0191191 A1* | 7/2012 | Trieu ............... A61B 17/683 623/17.11 |
| 2012/0197311 A1 | 8/2012 | Kirschman |
| 2012/0253398 A1 | 10/2012 | Metcalf et al. |
| 2012/0259372 A1 | 10/2012 | Glazer et al. |
| 2012/0271424 A1 | 10/2012 | Crawford |
| 2012/0296428 A1 | 11/2012 | Donner |
| 2012/0323285 A1 | 12/2012 | Assell et al. |
| 2013/0018427 A1 | 1/2013 | Pham et al. |
| 2013/0030456 A1 | 1/2013 | Assell et al. |
| 2013/0030529 A1 | 1/2013 | Hunt |
| 2013/0035727 A1 | 2/2013 | Datta |
| 2013/0053852 A1 | 2/2013 | Greenhalgh et al. |
| 2013/0053854 A1 | 2/2013 | Schoenefeld et al. |
| 2013/0053902 A1 | 2/2013 | Trudeau |
| 2013/0053963 A1 | 2/2013 | Davenport |
| 2013/0085535 A1 | 4/2013 | Greenhalgh et al. |
| 2013/0096683 A1* | 4/2013 | Kube, II ............... A61F 2/442 623/17.16 |
| 2013/0116793 A1* | 5/2013 | Kloss ............... A61F 2/4455 623/17.16 |
| 2013/0123850 A1 | 5/2013 | Schoenefeld et al. |
| 2013/0123935 A1 | 5/2013 | Hunt et al. |
| 2013/0131678 A1 | 5/2013 | Dahners |
| 2013/0144343 A1* | 6/2013 | Arnett ............... A61B 17/70 606/279 |
| 2013/0158609 A1 | 6/2013 | Mikhail et al. |
| 2013/0172736 A1 | 7/2013 | Abdou |
| 2013/0190614 A1 | 7/2013 | Swofford |
| 2013/0197590 A1 | 8/2013 | Assell et al. |
| 2013/0203088 A1 | 8/2013 | Baerlecken et al. |
| 2013/0218215 A1 | 8/2013 | Ginn et al. |
| 2013/0218282 A1* | 8/2013 | Hunt ............... A61F 2/3601 623/19.11 |
| 2013/0231746 A1 | 9/2013 | Ginn et al. |
| 2013/0237988 A1 | 9/2013 | Mauldin |
| 2013/0245703 A1 | 9/2013 | Warren et al. |
| 2013/0245763 A1 | 9/2013 | Mauldin |
| 2013/0267836 A1* | 10/2013 | Mauldin ............... A61B 6/12 600/424 |
| 2013/0267961 A1* | 10/2013 | Mauldin ............... A61B 17/8872 606/99 |
| 2013/0267989 A1 | 10/2013 | Mauldin et al. |
| 2013/0296953 A1* | 11/2013 | Mauldin ............... A61B 17/84 606/328 |
| 2014/0012340 A1 | 1/2014 | Beck et al. |
| 2014/0031934 A1 | 1/2014 | Trieu |
| 2014/0031935 A1 | 1/2014 | Donner et al. |
| 2014/0031939 A1* | 1/2014 | Wolfe ............... A61F 2/4455 623/17.16 |
| 2014/0046380 A1* | 2/2014 | Asfora ............... A61B 17/1615 606/304 |
| 2014/0074175 A1 | 3/2014 | Ehler et al. |
| 2014/0088596 A1 | 3/2014 | Assell et al. |
| 2014/0088707 A1* | 3/2014 | Donner ............... A61B 17/68 623/17.11 |
| 2014/0121776 A1 | 5/2014 | Hunt |
| 2014/0135927 A1* | 5/2014 | Pavlov ............... A61F 2/4455 623/17.11 |
| 2014/0142700 A1* | 5/2014 | Donner ............... A61F 2/44 623/17.11 |
| 2014/0200618 A1 | 7/2014 | Donner et al. |
| 2014/0207240 A1 | 7/2014 | Stoffman et al. |
| 2014/0222150 A1 | 8/2014 | Reiley |
| 2014/0257294 A1 | 9/2014 | Gedet et al. |
| 2014/0257408 A1 | 9/2014 | Trieu et al. |
| 2014/0257415 A1* | 9/2014 | Reiley ............... A61B 17/7055 606/329 |
| 2014/0276846 A1 | 9/2014 | Mauldin et al. |
| 2014/0276851 A1* | 9/2014 | Schneider ............... A61B 17/846 606/84 |
| 2014/0277165 A1 | 9/2014 | Katzman et al. |
| 2014/0277460 A1 | 9/2014 | Schifano et al. |
| 2014/0277462 A1* | 9/2014 | Yerby ............... A61F 2/4455 623/17.11 |
| 2014/0277463 A1* | 9/2014 | Yerby ............... A61F 2/32 623/17.11 |
| 2014/0288605 A1* | 9/2014 | Mesiwala ............... A61B 17/7055 606/279 |
| 2014/0288649 A1* | 9/2014 | Hunt ............... A61F 2/447 623/16.11 |
| 2014/0288650 A1* | 9/2014 | Hunt ............... A61F 2/30907 623/16.11 |
| 2014/0296982 A1 | 10/2014 | Cheng |
| 2014/0330382 A1 | 11/2014 | Mauldin |
| 2014/0364917 A1 | 12/2014 | Sandstrom et al. |
| 2015/0005832 A1 | 1/2015 | Reiley |
| 2015/0012051 A1 | 1/2015 | Warren et al. |
| 2015/0039037 A1 | 2/2015 | Donner et al. |
| 2015/0080951 A1* | 3/2015 | Yeh ............... A61B 17/7059 606/249 |
| 2015/0080972 A1 | 3/2015 | Chin et al. |
| 2015/0094765 A1 | 4/2015 | Donner et al. |
| 2015/0105828 A1 | 4/2015 | Reckling et al. |
| 2015/0112444 A1 | 4/2015 | Aksu |
| 2015/0150683 A1 | 6/2015 | Donner et al. |
| 2015/0173805 A1 | 6/2015 | Donner et al. |
| 2015/0173904 A1 | 6/2015 | Stark |
| 2015/0182268 A1* | 7/2015 | Donner ............... A61B 17/8066 606/281 |
| 2015/0190149 A1 | 7/2015 | Assell et al. |
| 2015/0190187 A1 | 7/2015 | Parent et al. |
| 2015/0216566 A1 | 8/2015 | Mikhail et al. |
| 2015/0238203 A1 | 8/2015 | Asfora |

(56) References Cited

U.S. PATENT DOCUMENTS

| | | |
|---|---|---|
| 2015/0250595 A1 | 9/2015 | Mauldin et al. |
| 2015/0250611 A1 | 9/2015 | Schifano et al. |
| 2015/0250612 A1 | 9/2015 | Schifano et al. |
| 2015/0313720 A1 | 11/2015 | Lorio |
| 2015/0320450 A1 | 11/2015 | Mootien et al. |
| 2015/0320451 A1 | 11/2015 | Mootien et al. |
| 2015/0320469 A1 | 11/2015 | Biedermann et al. |
| 2015/0342753 A1 | 12/2015 | Donner et al. |
| 2015/0351923 A1 | 12/2015 | Emstad |
| 2016/0000488 A1 | 1/2016 | Cross, III |
| 2016/0022429 A1 | 1/2016 | Greenhalgh et al. |
| 2016/0081809 A1* | 3/2016 | Schneider .............. A61B 17/84 623/17.11 |
| 2016/0081810 A1* | 3/2016 | Reiley ................ A61B 17/1604 623/17.11 |
| 2016/0095721 A1 | 4/2016 | Schell et al. |
| 2016/0100870 A1* | 4/2016 | Lavigne ............ A61B 17/7064 606/304 |
| 2016/0106477 A1 | 4/2016 | Hynes et al. |
| 2016/0106479 A1 | 4/2016 | Hynes et al. |
| 2016/0120661 A1 | 5/2016 | Schell et al. |
| 2016/0143671 A1 | 5/2016 | Jimenez |
| 2016/0175113 A1 | 6/2016 | Lins |
| 2016/0184103 A1* | 6/2016 | Fonte ................... A61L 27/306 623/23.5 |
| 2016/0242820 A1 | 8/2016 | Whipple et al. |
| 2016/0249940 A1 | 9/2016 | Stark |
| 2016/0278818 A1* | 9/2016 | Donner ............. A61B 17/7055 |
| 2016/0278819 A1* | 9/2016 | Donner ............. A61B 17/7055 |
| 2016/0287171 A1* | 10/2016 | Sand ................... A61B 5/4851 |
| 2016/0287301 A1 | 10/2016 | Mehl et al. |
| 2016/0302941 A1* | 10/2016 | Reiley .................... A61F 2/447 |
| 2016/0310188 A1 | 10/2016 | Marino et al. |
| 2016/0310197 A1 | 10/2016 | Black et al. |
| 2016/0324643 A1 | 11/2016 | Donner et al. |
| 2016/0374727 A1 | 12/2016 | Greenhalgh et al. |
| 2017/0007409 A1 | 1/2017 | Mauldin et al. |
| 2017/0020585 A1 | 1/2017 | Harshman et al. |
| 2017/0049488 A1 | 2/2017 | Vestgaarden |
| 2017/0128214 A1 | 5/2017 | Mayer |
| 2017/0135733 A1 | 5/2017 | Donner et al. |
| 2017/0143513 A1 | 5/2017 | Sandstrom et al. |
| 2017/0181770 A1 | 6/2017 | Reiley et al. |
| 2017/0209155 A1 | 7/2017 | Petersen |
| 2017/0224393 A1 | 8/2017 | Lavigne et al. |
| 2017/0246000 A1 | 8/2017 | Pavlov et al. |
| 2017/0273729 A1 | 9/2017 | Reiley |

FOREIGN PATENT DOCUMENTS

| | | |
|---|---|---|
| CN | 1909848 A | 2/2007 |
| CN | 101795632 A | 8/2010 |
| CN | 102361601 A | 2/2012 |
| EP | 1287796 A1 | 3/2003 |
| JP | 59200642 A | 11/1984 |
| JP | 05-176942 A | 7/1993 |
| JP | 05184615 A | 7/1993 |
| JP | 09149906 A | 10/1997 |
| JP | 10-85231 A | 4/1998 |
| JP | 11318931 A | 11/1999 |
| JP | 2002509753 A | 4/2002 |
| JP | 2003511198 A | 3/2003 |
| JP | 2003533329 A | 11/2003 |
| JP | 2003534046 A | 11/2003 |
| JP | 2004121841 | 4/2004 |
| JP | 2004512895 | 4/2004 |
| JP | 2004516866 | 6/2004 |
| JP | 2006506181 | 2/2006 |
| JP | 2008540036 A | 11/2008 |
| JP | 2009521990 A | 6/2009 |
| JP | 2010137016 A | 6/2010 |
| WO | WO97/31517 A2 | 8/1997 |
| WO | WO 01/17445 A1 | 3/2001 |
| WO | WO02/38054 | 5/2002 |
| WO | WO03/007839 A2 | 1/2003 |
| WO | WO2004/02344 A1 | 1/2004 |
| WO | WO2004/043277 A1 | 5/2004 |
| WO | WO2005/009729 A2 | 2/2005 |
| WO | WO2006/003316 | 1/2006 |
| WO | WO2006/023793 A2 | 3/2006 |
| WO | WO2009/029074 A1 | 3/2009 |
| WO | WO2010/105196 A1 | 9/2010 |
| WO | WO2011/110865 A2 | 9/2011 |
| WO | WO2011/149557 A1 | 12/2011 |
| WO | WO2013/000071 A1 | 1/2013 |
| WO | WO2013/119907 A1 | 8/2013 |

OTHER PUBLICATIONS

Al-Khayer et al.; Percutaneous sacroiliac joint arthrodesis, a novel technique; J Spinal Disord Tech; vol. 21; No. 5; pp. 359-363; Jul. 2008.

Khurana et al.; Percutaneous fusion of the sacroiliac joint with hollow modular anchorage screws, clinical and radiological outcome; J Bone Joint Surg; vol. 91-B; No. 5; pp. 627-631; May 2009.

Lu et al.; Mechanical properties of porous materials; Journal of Porous Materials; 6(4); pp. 359-368; Nov. 1, 1999.

Peretz et al.; The internal bony architecture of the sacrum; Spine; 23(9); pp. 971-974; May 1, 1998.

Richards et al.; Bone density and cortical thickness in normal, osteopenic, and osteoporotic sacra; Journal of Osteoporosis; 2010(ID 504078); 5 pgs; Jun. 9, 2010.

Wise et al.; Minimally invasive sacroiliac arthrodesis, outcomes of a new technique; J Spinal Disord Tech; vol. 21; No. 8; pp. 579-584; Dec. 2008.

Reiley, Mark A.; U.S. Appl. No. 12/357,483 entitled "Systems and methods for the fixation or fusion of bone in the hand and wrist," filed Jan. 22, 2009 (abandoned).

Reckling et al.; U.S. Appl. No. 15/838,070 entitled "Implant placement," filed Dec. 11, 2017.

Mesiwala et al.; U.S. Appl. No. 15/903,410 entitled "Implants for spinal fixation or fusion," filed Feb. 23, 2018.

Reiley et al.; U.S. Appl. No. 15/952,102 entitled "Apparatus, systems, and methods for the fixation or fusion of bone," filed Apr. 12, 2018.

* cited by examiner

(Anterior)

(Posterior)

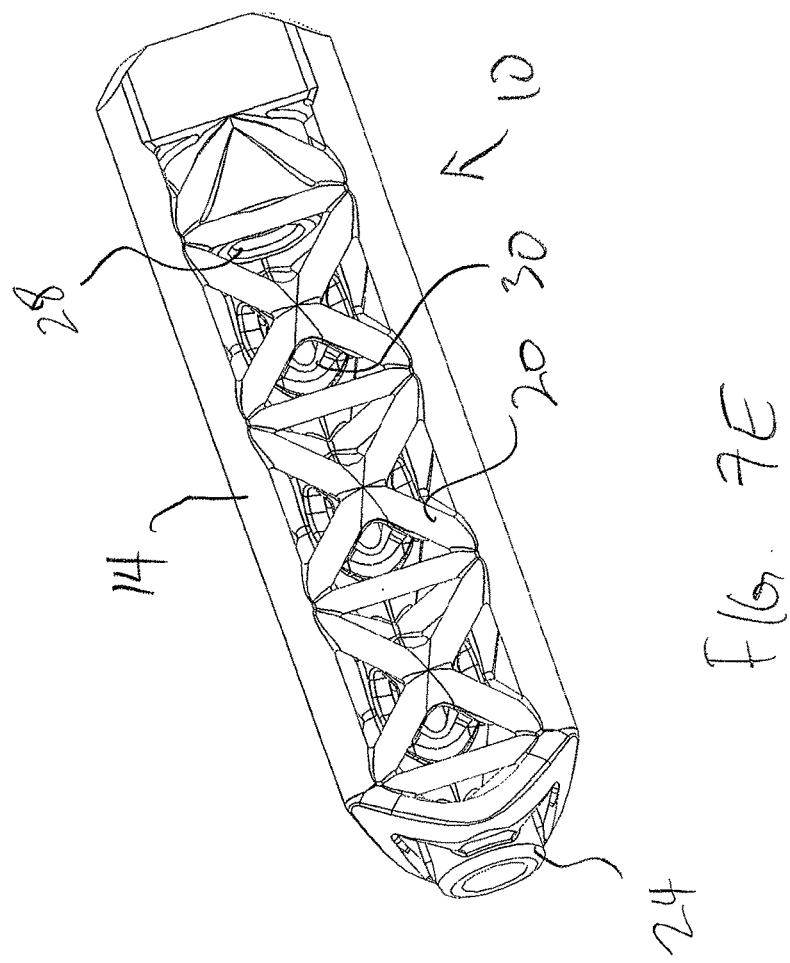

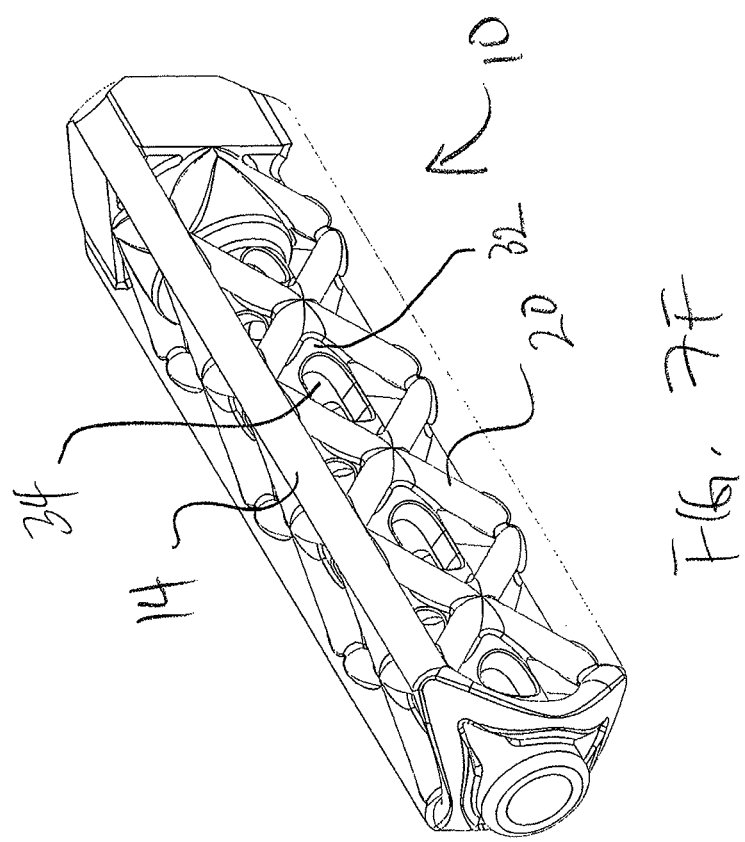

MATRIX IMPLANT

CROSS REFERENCE TO RELATED APPLICATIONS

This application is a continuation of U.S. patent application Ser. No. 14/859,005, filed Sep. 18, 2015, now U.S. Patent Application Publication No. 2016/0081809, which claims priority to U.S. Provisional Patent Application No. 62/052,379, filed Sep. 18, 2014, each of which is herein incorporated by reference in its entirety for all purposes.

INCORPORATION BY REFERENCE

All publications and patent applications mentioned in this specification are herein incorporated by reference to the same extent as if each individual publication or patent application was specifically and individually indicated to be incorporated by reference.

FIELD

Embodiments of the invention relate generally to bone implants that can be used to fuse two bone segments together.

BACKGROUND

Many types of hardware are available both for the fixation of bones that are fractured and for the fixation of bones that are to be fused (arthrodesed).

For example, the human hip girdle (see FIGS. 1 and 2) is made up of three large bones joined by three relatively immobile joints. One of the bones is called the sacrum and it lies at the bottom of the lumbar spine, where it connects with the L5 vertebra. The other two bones are commonly called "hip bones" and are technically referred to as the right ilium and-the left ilium. The sacrum connects with both hip bones at the sacroiliac joint (in shorthand, the SI-Joint).

The SI-Joint functions in the transmission of forces from the spine to the lower extremities, and vice-versa. The SI-Joint has been described as a pain generator for up to 22% of lower back pain patients.

To relieve pain generated from the SI-Joint, sacroiliac joint fusion is typically indicated as surgical treatment, e.g., for degenerative sacroiliitis, inflammatory sacroiliitis, iatrogenic instability of the sacroiliac joint, osteitis condensans ilii, or traumatic fracture dislocation of the pelvis. Currently, screws and screws with plates are used for sacro-iliac fusion. At the same time the cartilage has to be removed from the "synovial joint" portion of the SI-Joint. This requires a large incision to approach the damaged, subluxed, dislocated, fractured, or degenerated joint. The large incision and removal of tissue can cause significant trauma to the patient, resulting in pain and increasing the time to heal after surgery.

In addition, screw type implants tend to be susceptible to rotation and loosening, especially in joints that are subjected to torsional forces, such as the SI-Joint. Excessive movement of the implant after implantation may result in the failure of the implant to incorporate and fuse with the bone, which may result in the need to remove and replace the failed implant.

Consequently, it would be desirable to provide an implant for bone fusion or fixation that resists rotation, can be implanted using a minimally invasive procedure, and/or that can be used to rescue a failed implant.

SUMMARY OF THE DISCLOSURE

The present invention relates generally to bone implants that can be used to fuse two bone segments together.

In some embodiments, an implant for the fixation or fusion of the SI-Joint is provided. The implant can include an elongate body having a longitudinal axis and a rectilinear cross-sectional profile transverse to the longitudinal axis, the elongate body having a proximal end and a distal end. The elongate body can include a plurality of apex struts aligned with the longitudinal axis and extending between the proximal end and the distal end of the elongate body; a plurality of support struts that extend from one apex strut to another apex strut to form a matrix structure; and a first guide pin receptacle located along the longitudinal axis of the elongate body.

In some embodiments, the rectilinear cross-sectional profile is triangular.

In some embodiments, the rectilinear cross-sectional profile is rectangular or square.

In some embodiments, the elongate body is curved along the longitudinal axis from the proximal end to the distal end of the elongate body. In some embodiments, the elongate body has a curvature between about 5 and 45 degrees.

In some embodiments, the elongate body has a curvature between about 15 and 30 degrees.

In some embodiments, the guide pin receptacle has a circular opening adapted to securely receive a guide pin.

In some embodiments, the elongate body is coated with a titanium plasma spray.

In some embodiments, the elongate body is coated with hydroxyapatite.

In some embodiments, the elongate body is made of metal.

In some embodiments, the metal is titanium.

In some embodiments, the metal comprises a lattice structure.

In some embodiments, the lattice structure is cubic.

In some embodiments, the lattice structure is hexagonal.

In some embodiments, the lattice structure comprises a plurality of beams with a diameter between about 100 to 1000 microns.

In some embodiments, the elongate body is made of a ceramic material.

In some embodiments, the elongate body is mode of a plastic material.

In some embodiments, the elongate body has a porous outer surface.

In some embodiments, all struts are covered in a porous surface.

In some embodiments, all struts are preferentially covered in a porous surface.

In some embodiments, the porous outer surface has a pore size between about 100 to 1000 microns.

In some embodiments, the thickness of the apex struts and the support struts is between about 1 to 5 mm.

In some embodiments, the first guide pin receptacle is located at the distal end of the elongate body.

In some embodiments, the first guide pin receptacle is located at the proximal end of the elongate body.

In some embodiments, the first guide pin receptacle is located at the distal end of the elongate body and a second guide pin receptacle is located at the proximal end of the body.

In some embodiments, the implant can further include a continuous cannula extending between the first guide pin receptacle and the second guide pin receptacle.

In some embodiments, a third guide pin receptacle is located between the first guide pin receptacle and the second guide pin receptacle.

In some embodiments, a plurality of pin receptacles are located between the first guide pin receptacle and the second guide pin receptacle.

In some embodiments, a modular implant for the fixation or fusion of the SI-Joint is provided. The modular implant includes a distal portion comprising a frame, the frame joined to a distal guide pin receptacle and to a plurality of transverse support struts arranged in a rectilinear configuration; a proximal portion comprising a frame joined to a proximal guide pin receptacle and to a plurality of transverse support struts arranged in a rectilinear configuration; and at least one repeating internal portion. The at least one repeating internal portion comprises a plurality of apex struts joined together by oblique support struts arranged in an oblique configuration between the apex struts, a plurality of transverse support struts arranged perpendicularly to the apex struts, the plurality of transverse support struts arranged in a rectilinear configuration at both a proximal end and a distal end of the repeating internal portion, and an internal guide pin receptacle secured to the support struts and aligned with both the distal guide pin receptacle and the proximal guide pin receptacle; wherein the at least one internal repeating portion is positioned between the distal portion and the proximal portion such that the transverse support struts of the distal portion are aligned with a first set of transverse support struts of the repeating internal portion and the transverse support struts of the proximal portion are aligned with the a second set of transverse support struts of the repeating internal portion.

In some embodiments, the oblique supports struts are arranged in an "X" configuration. In some embodiments, the oblique supports struts are arranged in a non-overlapping diagonal configuration.

In some embodiments, the apex and support struts are arranged and spaced to accept bone graft material from the outer surface toward the center of the implant.

In some embodiments, the graft material is autograft.

In some embodiments, the graft material is allograft.

In some embodiments, the graft material is bone morphogenetic protein.

In some embodiments, the implant does not have any struts that extend from the outer surface toward the center of the implant, thereby forming a cavity for receiving a graft material and/or guide pin.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 7D-7F illustrate various embodiments of implants having a matrix structure with a plurality of pin receptacles.

DETAILED DESCRIPTION

Figure 1:
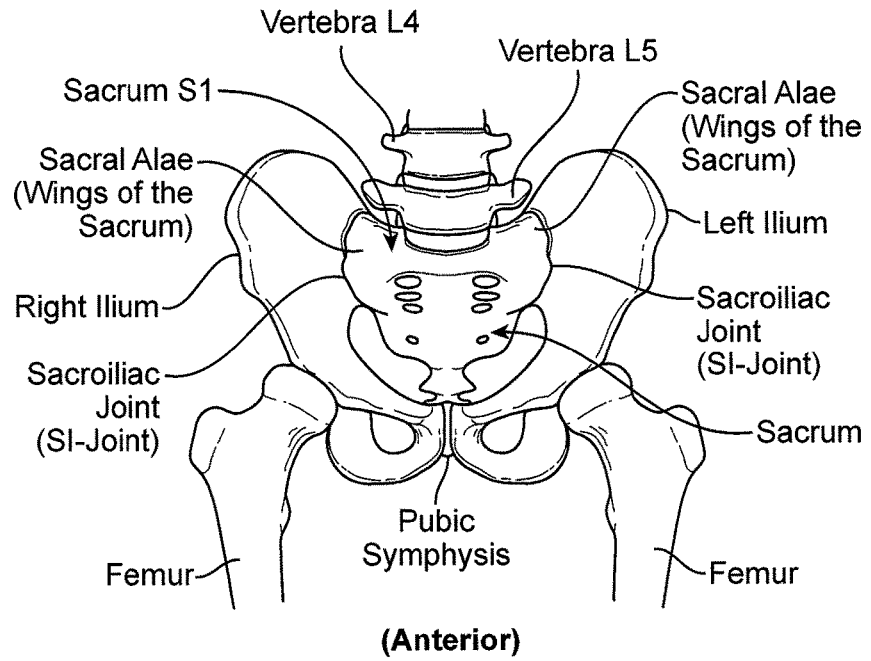
FIGS. 1 and 2 are, respectively, anterior and posterior anatomic views of the human hip girdle comprising the sacrum and the hip bones (the right ilium, and the left ilium), the sacrum being connected with both hip bones at the sacroiliac joint (in shorthand, the SI-Joint).
Figure 2:
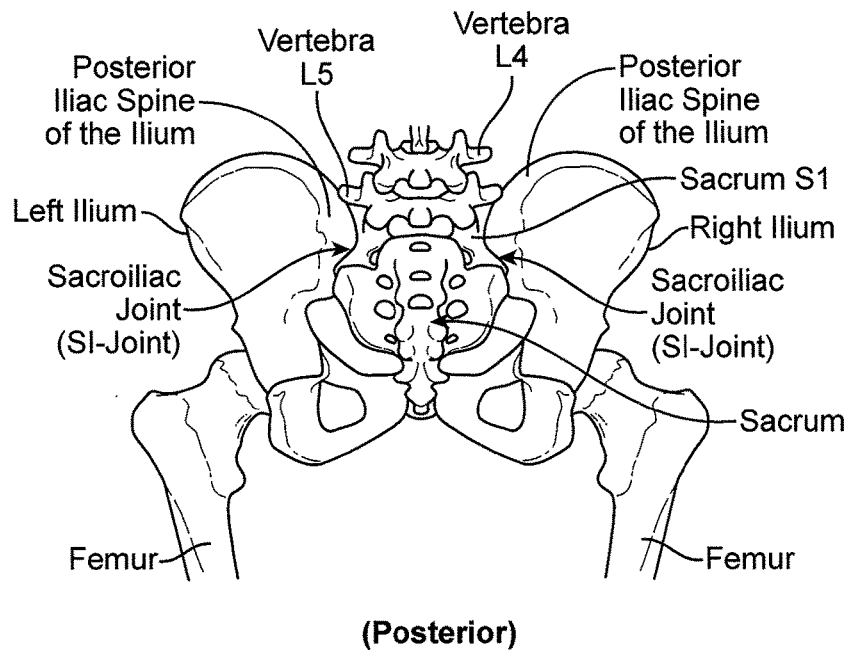
Figures 3, 4:
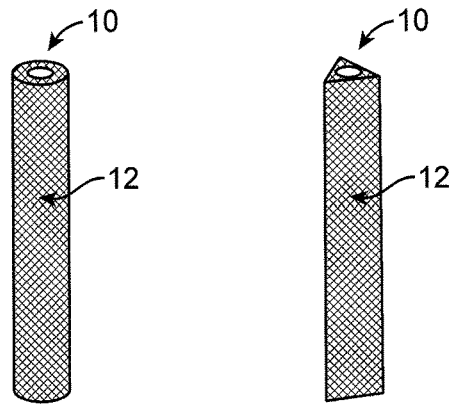
FIGS. 3 and 4 are embodiments of various straight implants that can be used for the fusion or fixation of a joint or two bone segments.

FIG. 3 and FIG. 4 illustrate straight implants 10 with a solid elongate body 12 that can be used for the fixation or fusion of two bone segments. The implant 10 shown in FIG. 3 is cylindrical and can optionally have screw threads along the exterior of the implant body. As mentioned above, cylindrical screw type implants can suffer from excessive rotation. One solution to this problem is the implant 10 in FIG. 4, which has a non-cylindrical cross-sectional area. For example, as shown, the implant 10 can have a triangular cross-sectional area, although other rectilinear cross-sectional profiles may be used as well, including rectangular, hexagonal and the like. Non-cylindrical implants need not have a strict rectilinear cross-sectional profile in order to resist rotation. A cross-sectional area that is non-circular will generally suffice. For example, a tear drop shaped cross-sectional area, or a cross-sectional area with at least one apex, can resist rotation. Other non-circular cross-sectional geometries that may not have a rectilinear component can also work, such as oval cross-sections.

Figure 5:
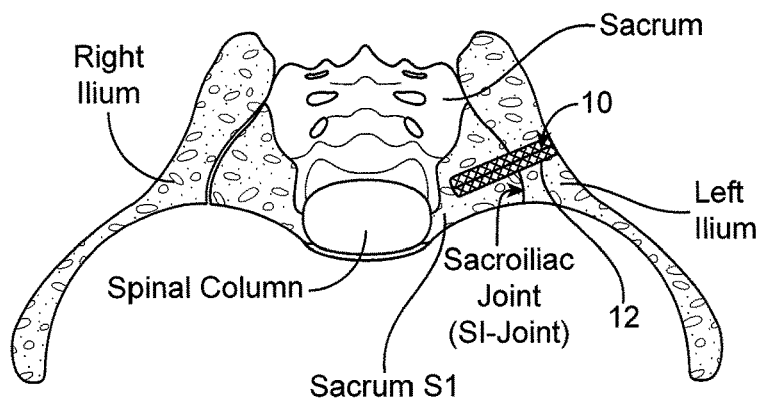
FIG. 5 illustrates an axial section view of the SI-Joint with an implant for the fixation of the SI-Joint using a lateral approach that goes laterally through the ilium, the SI-Joint, and into the sacrum S1.
Figure 6:
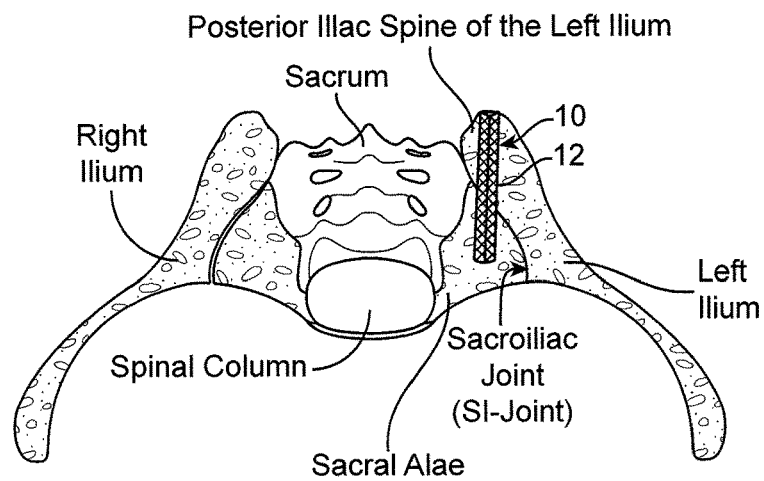
FIG. 6 illustrates an axial section view of the SI-Joint with an implant for the fixation of the SI-Joint using a postero-lateral approach entering from the posterior iliac spine of the ilium, angling through the SI-Joint, and terminating in the sacral alae.

FIG. 5 illustrates insertion of the implant 10 of FIG. 3 or FIG. 4 across the SI-Joint using a lateral approach that goes laterally through the ilium, across the SI-Joint, and into the sacrum. FIG. 6 illustrates insertion of the same implant across the SI-Joint using a postero-lateral approach entering from the posterior iliac spine of the ilium, angling through the SI-Joint, and terminating in the sacral alae. Many of the implants described herein can be inserted across the SI-Joint in a similar manner.

Matrix Implant

In some embodiments, it may be desirable to provide an implant with an open frame structure that can be packed with bone graft material and/or a biologic aid, while providing enough strength to facilitate the fusion of a joint or two bone segments without implant bending or failure.

One way to provide an open frame structure is to construct the elongate body 12 of the implant 10 using a matrix structure, as illustrated in FIGS. 7A-7C and 7G-7I. In some embodiments, each face or side of the elongate body 12 can be constructed using a matrix structure. The implant 10 can have a rectilinear overall cross-sectional profile transverse to a longitudinal axis that extends through the length of the elongate body 12. Each corner or apex of elongate body 12 can be formed with an apex strut 14 that extends between the proximal end 16 and the distal end 18 of the elongate body 12. An implant with a triangular overall cross-sectional profile has three apex struts, while an implant with a square or rectangular overall cross-sectional profile has four apex struts, and so on. To form the faces of the implant, support struts 20 can be arranged in various matrix structures.

Figure 7A:
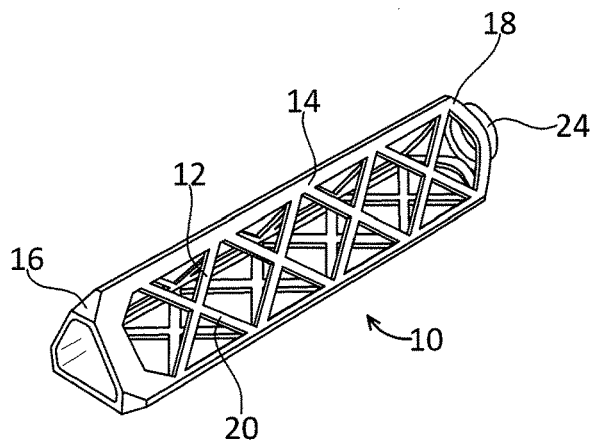
FIGS. 7A-7C illustrate various embodiments of implants having a matrix structure formed from a plurality of struts.

For example, FIG. 7A illustrates one embodiment of a matrix structure where the support struts 20 extend diagonally between two apex struts 14 and cross each other in an "X" configuration such that the support struts 20 define triangular and square openings. Additional transverse support struts that extend between two apex struts at a right angle to both apex struts can also be added. The transverse support struts can be positioned between the "X" support struts and/or can be positioned to cross the middle or intersection of the "X" support struts.

Figure 7B:
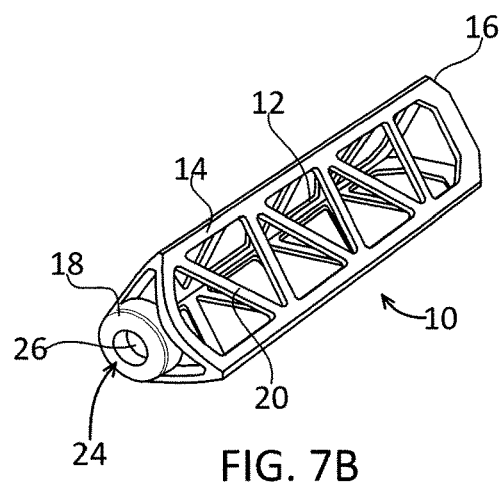

FIG. 7B illustrates another embodiment of a matrix structure where the support struts 20 are arranged in an alternating diagonal and transverse pattern. In this embodiment, the diagonal support struts on one face of the implant are all angled in the same direction such that the diagonal support struts are parallel to each other. The support struts 20 define triangular openings.

Figure 7C:
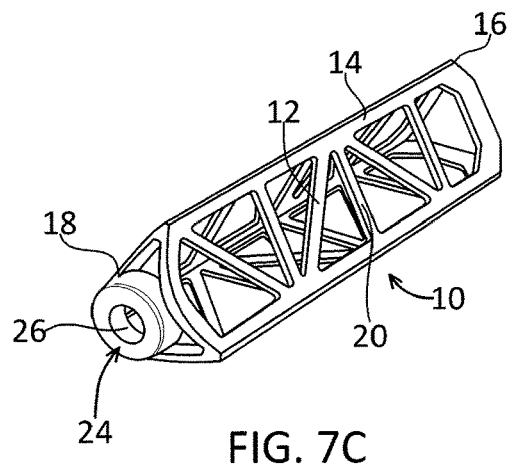

FIG. 7C illustrates yet another embodiment of a matrix structure where the support struts 20 are arranged in an alternating diagonal and transverse pattern. In this embodiment, the diagonal support struts are angled in an alternating pattern such that the diagonal support struts are oriented about 90 degrees to one another to form a zigzag pattern. The support struts 20 also define triangular openings.

The various matrix structures can provide different levels of resistance to various forces that the implant will be subjected to, including compressive, tensile, shear, bending, and torsional forces.

Figure 8:
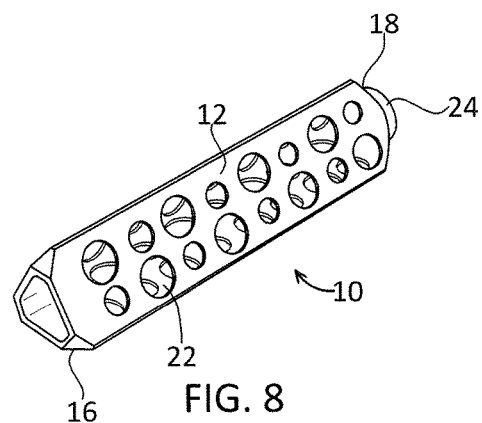
FIG. 8 illustrates an embodiment of a fenestrated implant.

FIG. 8 illustrates an alternative to using a matrix structure to provide openings. The implant 10 can have an elongate body 12 with fenestrations 22. The fenestrations 22 can be circular as shown, and can be of different sizes in, for example, an alternating pattern of large and small fenestrations. The fenestrations 22 can alternatively be rectilinear in shape, such as triangular, square, rectangular, and the like, or curvilinear, such as elliptical, oval, or circular.

In some embodiments, the fenestrations 22 can be triangular, square, rectangular or combinations of the above and can be arranged to form a matrix structure. In other words, the openings in FIGS. 7A-7B defined by the support struts 20 can be considered fenestrations 22.

Figure 7D:
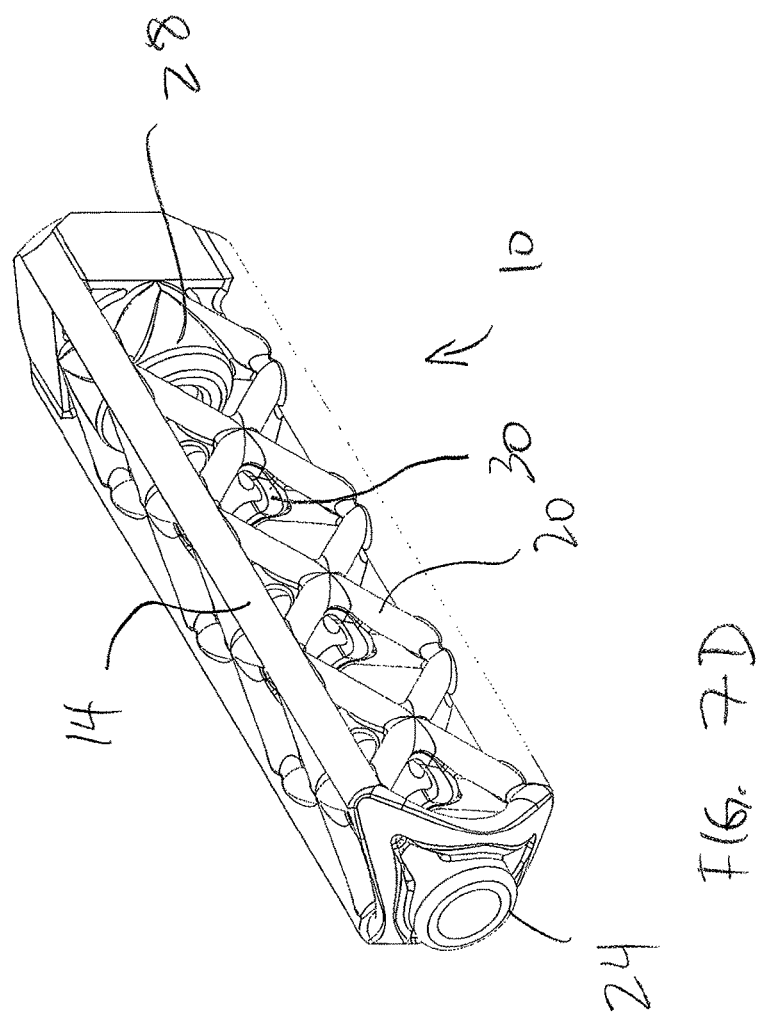
Figure 7G:
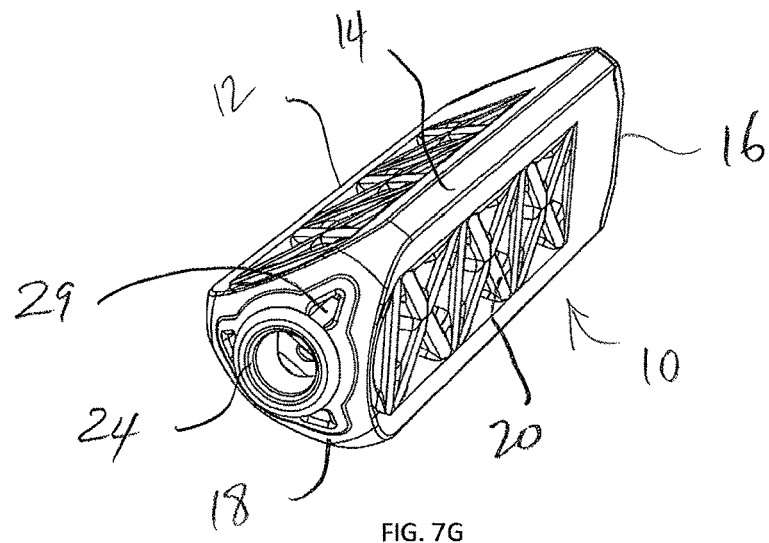
FIGS. 7G-7I illustrate another embodiment of an implant having a matrix structure from various angles and cross-sections.
Figure 7H:
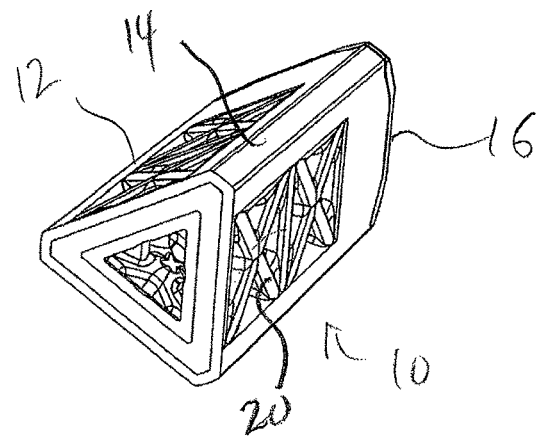
Figure 7I:
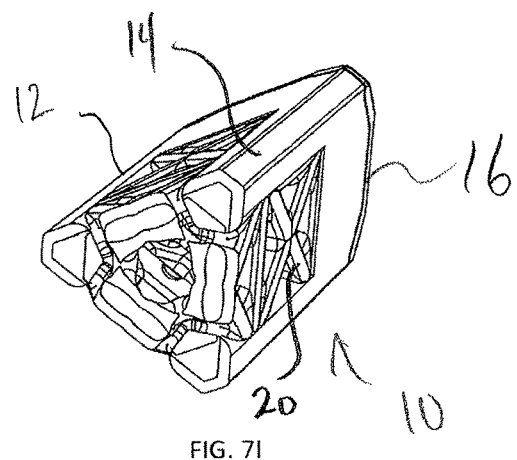

The walls of elongate body 12 can be planar and, as described above, can be formed from support struts 20 and/or fenestrations 22, as shown in FIGS. 7G-7I, for example. Using planar walls to form the elongate body 12 can result in a hollow cavity with the same or similar cross-sectional profile as the overall implant. For example, an implant with a triangular overall cross-sectional profile can also have a cavity with a triangular cross-sectional profile. The thickness of the walls and the apex struts and support struts can be between about 1 mm and 5 mm, or between about 1 and 3 mm. In addition, the distal ends of the walls can be tapered.

To facilitate the use of a traditional guide pin with these implants, the distal end of the implant can include a distal guide pin receptacle 24 with an opening 26 that is sized and shaped to receive a guide pin, as shown in FIGS. 7A-8. For example, the opening 26 can be circular to receive a typical guide pin. In some embodiments, the proximal end can additionally or alternatively have a proximal guide pin receptacle with an opening sized and shaped to receive a guide pin. In some embodiments, a continuous cannula can extend from the proximal guide pin receptacle to the distal guide pin receptacle. In some embodiments, multiple individual and co-linear guide pin receptacles can be present within the implant body between the proximal guide pin receptacle and the distal guide pin receptacle.

For example, FIG. 7D illustrates another embodiment of a matrix structure, similar to the embodiment shown in FIG. 7A, with support struts 20 that extend diagonally between apex struts 14 in an "X" configuration. However, in this embodiment, the implant 10 has a proximal guide pin receptacle 28 located at the proximal end of the implant, a distal guide pin receptacle 24 located at the distal end of the implant, and a plurality of internal guide pin receptacles 30 also located along the longitudinal axis of the implant. The internal guide pin receptacles 30 can be attached to the support struts 20 and/or apex struts 14. As shown, the internal guide pin receptacles 30 are attached at the intersection points of the "X" shaped support struts 20. In addition to receiving the guide pin, the internal guide pin receptacles 30 can provide additional support and bracing to the matrix structure.

FIG. 7E illustrates another embodiment of a matrix structure that is similar to the embodiment shown in FIG. 7D. Both embodiments have "X" shaped support struts 20 and a plurality of internal guide pin receptacles 30. However, this embodiment has additional support struts 20 that extend transversely between the apex struts 14 at right angles. The transverse support struts can be positioned between the "X" shaped support struts as shown, or can be integrated into the "X" shaped support struts. The transverse support struts can provide additional support and bracing to the matrix structure.

FIG. 7F illustrates another embodiment of a matrix structure that is similar to the embodiment shown in FIG. 7D. However, instead of having a plurality of guide pin receptacles, the implant 10 has a single guide pin receptacle 32 that extends from the proximal end to the distal end of the implant. This guide pin receptacle 32 can be a tube or cannula that can be attached to the support struts 20. In some embodiments, the tube or cannula can also have a plurality of fenestrations 34. In some embodiments, the fenestrations 34 can be positioned along the openings of the support struts, which allows the tube to support the support struts 20 while fenestrations promote bony ingrowth and allow the introduction of bone graft material through the implant.

FIGS. 7G-7I illustrates another embodiment of a matrix structure that is similar to the embodiment shown in FIG. 7E. This embodiment also has "X" shaped support struts 20 and additional support struts 20 that extend transversely between the apex struts 14 at right angles. One difference between this embodiment and the embodiment illustrated in FIG. 7E is that the support struts 20 and apex struts 14 in this embodiment have generally rectilinear cross-sectional profiles while the embodiment disclosed in FIG. 7E has generally circular support struts 20 and apex struts 14. In some embodiments, the apex struts 14 can be chamfered to remove sharp edges and the apices of the implant. In addition, this embodiment can have a distal guide pin receptacle 24 and a proximal guide pin receptacle, but unlike some of the embodiments described above, can lack internal guide pin receptacles. The guide pin can instead be supported internally by the inherent cross-sectional geometry of the apex struts and/or support struts. Any of the embodiments herein can have rectilinear, circular, or a combination of the two cross-sectional profiles. The use of the rectilinear struts may allow for the fabrication of the matrix implant by laser cutting a walled structure, while tubular struts may be welded together. A laser cut structure may be structurally stronger than a welded structure, which is important for supporting the large loads applied to the implant after implantation. The distal end 18 of the implant 10 can also have one or more openings 29 that allow graft material to be injected distally through the implant after implantation. In addition, any of the embodiments described herein can optionally have the internal guide pin receptacles, or omit the internal guide pin receptacles. FIG. 7H illustrates a cross-sectional view taken through the transverse struts, while FIG. 7I illustrates a cross-sectional view taken through the "X" shaped support struts.

Figure 9A:
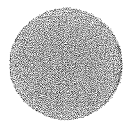
FIGS. 9A-9D illustrate various cross-sectional profiles of the implant microstructure, which can be formed with beam microstructures of varying geometries.
Figure 9B:
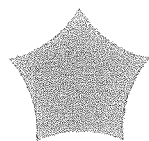
Figure 9C:
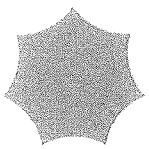
Figure 9D:
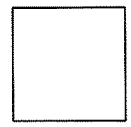

The implant, including the apex struts and/or support struts of the matrix as well as the beams that form the microstructure, can have a variety of shapes. For example, the beams and/or struts can have a cross-section that is rectilinear, curvilinear, or combinations of the two, as illustrated in FIGS. 9A-9D. For example, the beams and/or struts can have a circular cross-section as shown in FIG. 9A, or a curvilinear cross-section as shown in FIGS. 9B and 9C, or a square or rectangular cross section as shown in FIG. 9D. It should be understood that the corners and edges of the beams and/or struts can be rounded off if desired.

Figure 10A:
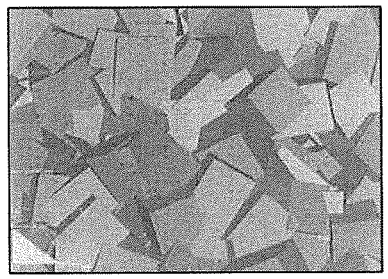
FIGS. 10A-10C illustrate various alternative beam microstructures.
Figure 10B:
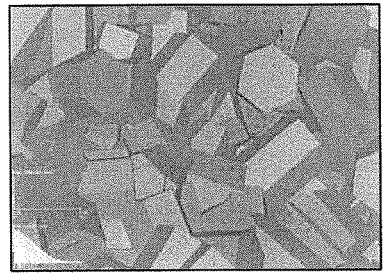
Figure 10C:
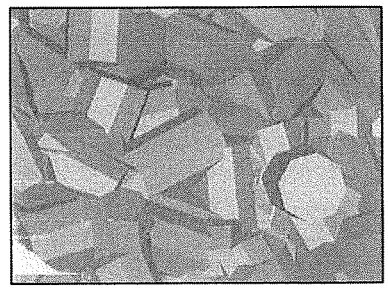
Figure 11A:
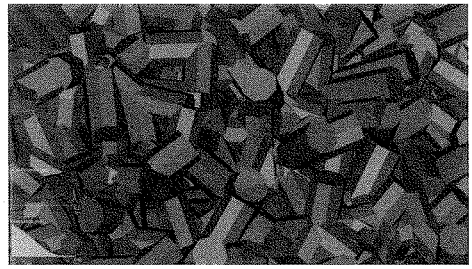
FIGS. 11A-11D illustrate various sizes for the beams that form the implant microstructure.
Figure 11B:
Figure 11C:
Figure 11D:

The implant can be made of a variety of materials. For example, the implant can be made of a metal or metal alloy, such as titanium or steel, or a nonmetallic material such as ceramic or polymer. In some embodiments, the implant material can have a certain lattice microstructure formed from the beam microparticles. For example, the lattice microstructure of the apex strut, support struts and other parts of the implant can result in a rough or smooth surface texture, depending on the surface finishing techniques used, such as polishing or application of a metal plasma spray, and the size and shape of the beams that form the lattice microstructure. For example, FIGS. 10A-10C illustrate various beam microstructures that can form the lattice microstructure. FIG. 10A illustrates a cubic beam structure, while FIG. 10B illustrates a hexagonal beam structure, and FIG. 10C illustrates an octagonal beam structure. Other beam structures include tetragonal, rhombohedral, orthorhombic, monoclinic, and triclinic. FIGS. 11A-11D illustrate that the beams can have various sizes. For example, FIGS. 11A-11D illustrate beams having a diameter of about 100, 200 microns, 350 microns, 500 microns, and 1000 microns. In other embodiments, the size of the beam can vary between 50 microns to 5000 microns.

The matrix implant can be manufactured using a variety of techniques. For example, the matrix implant can be 3-D printed using a rapid prototyping technique involving additive manufacturing, such as described in U.S. Patent Publication No. 2010/0161061, which is herein incorporated by reference in its entirety for all purposes. The 3-D printed matrix implant can be made of a metal, polymer, or ceramic material. For example, a metal powder such as titanium powder can be fused together to form the implant structure. Other techniques include cutting out the fenestrations or openings, using a laser for example, to form the apex struts and support struts, or using electric discharge machining (EDM) to create the matrixes or fenestrations.

3-D printing allows the porosity of the implant to be controlled. For example, the implant can have a volume porosity between about 30 and 70 percent, with an average pore size between 100 and 1000 microns. The pores can be largely interconnected, largely unconnected, or a mix of interconnected and unconnected pores. In some embodiments, the pores can be located throughout the material of the implant, including the apex struts and support struts, and on all or some of the strut surfaces, including the inner and outer implant surfaces. For example, the fusion of the beam microparticles to form the struts can result in a porous, semi-porous, or nonporous structure, depending on the degree of fusion between the beam microparticles. In other embodiments, the pores can be located in a porous coating that can be applied onto the implant. For example, a porous coating can be applied using a titanium plasma spray process, or another metal plasma spray process. The coating can be applied to the outer surfaces of the implant, the interior surfaces of the implant, or both the outer and interior surfaces of the implant. For example, the coating could be preferentially applied to the outer surface of a matrixed implant to provide bony ingrowth and ongrowth, and not applied to the inner portion of the implant to maximize bony through-growth within the implant. Also, the coating can be applied preferentially from proximal to distal, or vice versa. The thickness of a porous coating can be between about 500 and 1,500 microns. In addition or alternatively to the porous metal coating, a hydroxyapatite coating can also be applied to the implant. In some embodiments, the porosity can be varied along the length of the implant. In some embodiments, the thickness of the coating can be varied along the length of the implant. In some embodiments, the thickness of the coating applied to the outer surface can be different than the thickness of the inner coating. For example, the outer coating may be greater than the inner coating in some embodiments. In other embodiments, the thickness of the inner and outer coatings can be the same.

Figure 12:
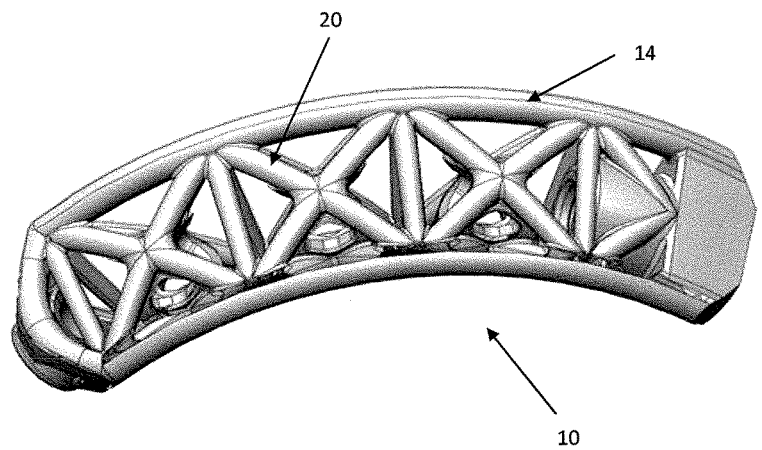
FIG. 12 illustrates an embodiment of a curved matrix implant.

In some embodiments, as illustrated in FIG. 12, the apex struts 14 can be curved from the proximal end to the distal end of the apex strut 14, thereby resulting in a curved matrix implant 10 similar to the curved implants described in U.S. Provisional Application No. 62/052,318, filed Sep. 18, 2014 and entitled "IMPLANTS FOR BONE FIXATION OR FUSION," which is herein incorporated by reference in its entirety for all purposes.

Figure 13:
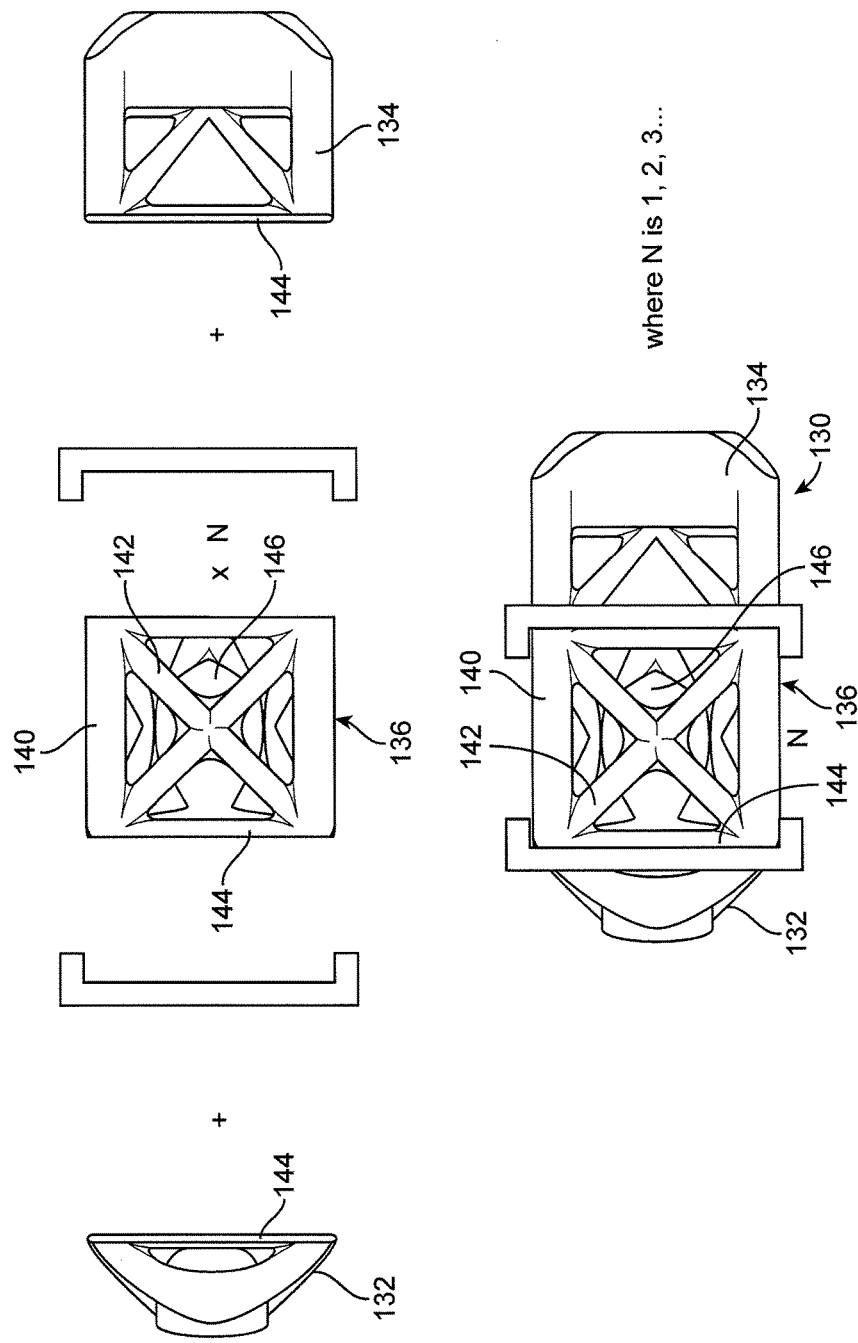
FIG. 13 illustrates an embodiment of a modular matrix implant.

The length of the implant can vary between about 25 to 95 mm. The matrix structure can be modular, as shown in FIG. 13, which allows the length of the implant to be varied by the addition of additional repeating subunits during the design and/or fabrication of the implant. For example, the modular matrix implant 130 can have a distal end portion 132, a proximal end portion 134, and one or more repeating internal portions 136. The distal end portion 132 can have a distal guide pin receptacle 138, and the proximal end portion 134 can have a proximal guide pin receptacle 136, much like the embodiments discussed above. The repeating internal portion 136 can have apex struts 140 and support struts 142, as described above. For example, as shown, the support struts 142 can have an "X" configuration and can be located between two transverse support struts 144. The two transverse support struts 144 can be half the normal transverse support struts such that when two repeating internal portions 136 are joined together, the two half support struts merge to form a whole transverse support strut. The proximal and distal end portions 132, 134 can also have a coupling portion that is formed from half transverse support struts 144 that can be merged with the half transverse support struts 144 of the repeating internal portion 136. In some embodiments, the repeating internal portion 136 can also have an internal guide pin receptacle 146

In some embodiments, the length of the repeating internal portion 136 can be about 10 mm. In other embodiments, the length can be between about 5 and 25 mm. In some embodiments, the repeating internal portion 136 can have support struts that form half an "X", such that the repeating internal portions are arranged in an alternating pattern to form "X" shaped support struts. In some embodiments, the support struts are simply diagonal struts that extend across the length of the repeating internal portion.

Methods of Implantation

The methods of implantation of the various implants described herein are described in U.S. Patent Publication No. 2011/0087294, U.S. Pat. No. 8,425,570, U.S. Pat. No. 8,444,693, U.S. Pat. No. 8,414,648, and U.S. Pat. No. 8,470,004, and U.S. Provisional Application No. 61/891,326, each of which is herein incorporated by reference in its entirety for all purposes. These methods are particularly suited for use with straight implants.

The curved implant illustrated in FIG. 12 may require modifications to the method of insertion protocols. Because the implant is curved, it may not be possible or desirable to attempt to hammer or tap the implant into the bone along a straight path using a straight guide pin, a straight drill, a straight broach and the like. Instead, it may be desirable to create and form a curved insertion path that matches the curvature of the implant.

For example, the tooling used to create the curved insertion path can have a radius of curvature that matches the radius of curvature of the implant. For example, some or all of the tooling and the implant can have a matching radius of curvature. The tooling, which can include a guide pin, a tool guide, a drill bit, a broach, and impact hammer and the like can be rotatably secured by an arm with a length equal to the radius of curvature, with one end of the arm attached to a pivot and the other end used to secure the tools and/or implant.

The rotating arm can be used to drive a curved guide pin into the bone to create a curved path through the bone, such as the ilium and the sacrum. A relatively short drill bit with a lumen for receiving the guide pin can be disposed over the curved guide pin to drill out a curved pilot bore. In some embodiments, the drill bit can be secured by the pivoting arm at the end of a curved guide and can be used to drill the curved pilot bore without the insertion of the curved guide pin.

For a curved implant with a circular cross section, the curved implant can then be advanced over the curved guide pin and into the curved insertion path that is formed by the curved pilot bore. In some embodiments, the curved implant can be held by the pivoting arm and inserted into the curved insertion path without the aid of a guide pin by rotating the curved arm.

For a rectilinear implant or more broadly a noncircular implant, the curved pilot bore can be shaped using an appropriately shaped broach that matches the overall cross-sectional shape of the implant. A curved broach, or a short broach, can be advanced over the curved guide pin if present, otherwise the curved broach or short broach can be held in the pivoting arm and advanced through the pilot bore by rotation of the pivoting arm. As the broach is advanced, it shapes the pilot bore into a shape that matches the shape of the implant.

The curved implant can then be advanced over the curved guide pin and into the curved insertion path that is formed by the curved pilot bore. In some embodiments, the curved implant can be held by the pivoting arm and inserted into the curved insertion path without the aid of a guide pin by rotating the curved arm.

More generally, the implants described herein can be used to fuse any two bone segments, such as two bones that form a joint or two bones resulting from a fracture.

The terms "about" and "approximately" and the like can mean within 5, 10, 15, 20, 25, or 30 percent.

It is understood that this disclosure, in many respects, is only illustrative of the numerous alternative device embodiments of the present invention. Changes may be made in the details, particularly in matters of shape, size, material and arrangement of various device components without exceeding the scope of the various embodiments of the invention. Those skilled in the art will appreciate that the exemplary embodiments and descriptions thereof are merely illustrative of the invention as a whole. While several principles of the invention are made clear in the exemplary embodiments described above, those skilled in the art will appreciate that modifications of the structure, arrangement, proportions, elements, materials and methods of use, may be utilized in the practice of the invention, and otherwise, which are particularly adapted to specific environments and operative requirements without departing from the scope of the invention. In addition, while certain features and elements have been described in connection with particular embodiments, those skilled in the art will appreciate that those features and elements can be combined with the other embodiments disclosed herein.

What is claimed is:

1. A modular implant for the fixation or fusion of the SI-Joint, the modular implant comprising:
   a distal portion comprising a distal guide pin receptacle;
   a proximal portion comprising a proximal guide pin receptacle; and
   at least one repeating internal portion comprising:
      a plurality of apex struts joined together by oblique support struts arranged in an oblique configuration between the apex struts, and
      a plurality of transverse support struts arranged perpendicularly to the apex struts, the plurality of transverse support struts arranged in a rectilinear configuration at both a proximal end and a distal end of the repeating internal portion;
   wherein the at least one internal repeating portion is positioned between the distal portion and the proximal portion.

2. The modular implant of claim 1, wherein the at least one repeating internal portion further comprises an internal guide pin receptacle secured to the oblique support struts and/or transverse support struts and aligned with both the distal guide pin receptacle and the proximal guide pin receptacle.

3. The modular implant of claim 1, wherein the oblique supports struts are arranged in an "X" configuration.

4. The modular implant of claim 1, wherein the oblique supports struts are arranged in a non-overlapping diagonal configuration.

5. The modular implant of claim 1, wherein the repeating internal portion has a rectilinear cross-sectional profile transverse to a longitudinal axis that extends from the proximal portion to the distal portion.

6. The modular implant of claim 5, wherein the rectilinear cross-sectional profile is triangular.

7. The modular implant of claim 5, wherein the rectilinear cross-sectional profile is rectangular or square.

* * * * *